US010006883B2

(12) United States Patent
Sugiyama et al.

(10) Patent No.: US 10,006,883 B2
(45) Date of Patent: Jun. 26, 2018

(54) PARTICULATE SENSOR

(71) Applicant: NGK SPARK PLUG CO., LTD., Nagoya-shi, Aichi (JP)

(72) Inventors: Takeshi Sugiyama, Ichinomiya (JP); Masayuki Motomura, Komaki (JP); Norimasa Osawa, Aichi (JP); Keisuke Tashima, Kasugai (JP); Hirokazu Murase, Nisshin (JP); Toshiya Matsuoka, Gifu (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 139 days.

(21) Appl. No.: 14/591,499

(22) Filed: Jan. 7, 2015

(65) Prior Publication Data
US 2015/0192545 A1 Jul. 9, 2015

(30) Foreign Application Priority Data

Jan. 8, 2014 (JP) ................................. 2014-001920

(51) Int. Cl.
*G01N 27/70* (2006.01)
(52) U.S. Cl.
CPC .................. *G01N 27/70* (2013.01)
(58) Field of Classification Search
CPC ..................................................... G01N 27/68
See application file for complete search history.

(56) References Cited

U.S. PATENT DOCUMENTS 6,634,210 B1* 10/2003 Bosch ............... G01N 15/0656
204/426
6,971,258 B2* 12/2005 Rhodes ............. G01N 15/0656
73/28.01

(Continued)

FOREIGN PATENT DOCUMENTS

JP 2010-151613 A 7/2010
JP 2013-170914 A 9/2013

(Continued)

OTHER PUBLICATIONS

Machine translation of JP2013-170914.*
Communication dated Jul. 4, 2017 from the Japanese Patent Office in counterpart application No. 2014-001920.

Primary Examiner — David Bolduc
(74) Attorney, Agent, or Firm — Sughrue Mion, PLLC

(57) ABSTRACT

A particulate sensor (1) includes an ion source (15) and a reference potential member (45). The particulate sensor (1) detects particulates S contained in a gas under measurement EG by means of ions CP. The ion source (15) includes a ceramic structure (100) having a ceramic laminate (101) and a discharge electrode member (110). The discharge electrode member (110) has an inter-layer portion (112A, 111) embedded between the layers of the ceramic laminate (101) and an exposed portion (112B) extending from the inter-layer portion (112A, 111) to a position outside the ceramic laminate (101). The discharge electrode member (110) generates the gaseous discharge between the reference potential member (45) and the exposed portion (112B) including one or more needle-shaped distal end portions (112S) upon application of a constant DC discharge potential PV2.

13 Claims, 9 Drawing Sheets

(56) References Cited

U.S. PATENT DOCUMENTS

| | | | |
|---|---|---|---|
| 7,998,417 B2* | 8/2011 | Hall | G01N 15/0656 422/83 |
| 8,161,796 B2* | 4/2012 | Nair | G01N 15/0656 73/23.33 |
| 2006/0016246 A1* | 1/2006 | Rhodes | F01N 11/00 73/28.01 |
| 2007/0119233 A1* | 5/2007 | Schnell | G01N 15/0656 73/28.01 |
| 2008/0190173 A1* | 8/2008 | Wienand | G01N 15/0656 73/28.01 |
| 2008/0202943 A1* | 8/2008 | Guenschel | G01N 15/0656 205/775 |
| 2009/0056416 A1* | 3/2009 | Nair | G01N 15/0656 73/28.01 |
| 2009/0126458 A1* | 5/2009 | Fleischer | G01N 15/0656 73/28.01 |
| 2009/0217737 A1* | 9/2009 | Dorfmueller | F01N 11/00 73/28.01 |
| 2010/0000404 A1 | 1/2010 | Sakuma et al. | |
| 2010/0000863 A1* | 1/2010 | Kondo | G01N 15/0656 204/406 |
| 2010/0071441 A1* | 3/2010 | Sakuma | G01N 15/0656 73/28.01 |
| 2010/0147052 A1* | 6/2010 | Nelson | G01N 15/0656 73/28.01 |
| 2010/0229629 A1* | 9/2010 | Egami | G01N 27/68 73/28.01 |
| 2010/0229630 A1* | 9/2010 | Tokuda | G01N 27/68 73/28.01 |
| 2010/0229724 A1* | 9/2010 | Tokuda | G01N 27/68 96/19 |
| 2011/0018546 A1* | 1/2011 | Kitano | G01N 27/68 324/464 |
| 2011/0187379 A1* | 8/2011 | Shinada | G01N 27/70 324/464 |
| 2011/0260732 A1* | 10/2011 | Shinada | G01N 27/70 324/464 |
| 2012/0234172 A1* | 9/2012 | Sugiyama | G01N 15/0656 96/26 |
| 2012/0262182 A1* | 10/2012 | Matsuoka | G01N 15/0656 324/464 |
| 2012/0285219 A1* | 11/2012 | Matuoka | F02D 41/1466 73/23.33 |
| 2013/0283887 A1* | 10/2013 | Ante | F01N 9/002 73/28.01 |
| 2014/0352405 A1* | 12/2014 | Motomura | G01N 15/0656 73/23.31 |
| 2015/0102822 A1 | 4/2015 | Okuda | |

FOREIGN PATENT DOCUMENTS

| | | |
|---|---|---|
| WO | 2008/111677 A1 | 9/2008 |
| WO | 2013/175548 A1 | 11/2013 |

* cited by examiner

PARTICULATE SENSOR

BACKGROUND OF THE INVENTION

1. Field of the Invention

The present invention relates to a particulate sensor for detecting particulates contained in a gas under measurement.

2. Description of the Related Art

Patent Document 1 discloses an example of a particulate sensor which can detect particulates contained in exhaust gas. Specifically, Patent Document 1 discloses a particulate sensor which generates ions by means of corona discharge, and electrifies (or charges) particulates contained in exhaust gas by action of the ions, to thereby detect the amount of particulates contained in the exhaust gas.

The particulate sensor disclosed in Patent Document 1 has a sensor unit in which first through fifth insulative ceramic layers each formed of an insulating ceramic are laminated. In this sensor unit, first and second ground patterns are disposed between the plurality of insulative ceramic layers, and a discharge pattern is formed on the surface of a second ceramic layer by pattern printing. Electric power (2 to 3 kV, 100 kHz) for corona discharge is supplied to a distal end portion (discharge electrode) of a discharge pattern, whereby a corona discharge is produced between the discharge pattern and the second ground pattern (see FIG. 6 of Patent Document 1).

[Patent Document 1] Japanese Patent Application Laid-Open (kokai) No. 2013-170914

3. Problems to be Solved by the Invention

In conventional particulate sensors, such as the particulate sensor of Patent Document 1, AC high voltage or pulsed DC high voltage has been applied between the electrodes in order to generate ions by means of corona discharge. The pulsed DC high voltage is obtained by half-wave rectifying AC high voltage or switching DC high voltage through on/off control, and contains a large AC voltage component.

However, in the case of gaseous discharge, such as corona discharge, generated by applying a high voltage, the use of AC high voltage or pulsed DC high voltage causes various problems. For example, the controllable frequency is restricted, expensive switching elements are needed, and control circuits become complex. This results in an increase in cost.

Meanwhile, in a sensor in which a ceramic laminate such as the sensor unit of Patent Document 1 is used, its insulating ceramic layer is a dielectric. Therefore, in the case where a discharge electrode is formed on the surface of the ceramic laminate, and a constant DC voltage whose voltage fluctuation is small; i.e., whose AC voltage component is small, is applied between the discharge electrode and a ground layer within the ceramic laminate, ions cannot be continuously generated by means of corona discharge.

SUMMARY OF THE INVENTION

The present invention has been accomplished in view of the above problem, and an object thereof is to provide a particulate sensor in which a discharge electrode is integrated with a ceramic laminate and which can produce gaseous discharge by applying a constant DC voltage to the discharge electrode.

The above object has been achieved by providing (1) a particulate sensor which includes an ion source for generating ions by gaseous discharge and a reference potential member disposed around the ion source and maintained at a reference potential and which detects particulates contained in a gas under measurement by means of a current signal corresponding to a charge amount of ions discharged from the sensor in the form of charged particulates which result from ions adhering to the particulates. The ion source comprises a ceramic structure which includes a ceramic laminate of a plurality of insulative ceramic layers; and a discharge electrode member having an inter-layer portion embedded between two of the ceramic layers of the ceramic laminate and an exposed portion extending from the inter-layer portion to a position outside the ceramic laminate, the discharge electrode member generating the gaseous discharge between the reference potential member and the exposed portion when a constant DC discharge potential is applied to the discharge electrode member. The exposed portion of the discharge electrode member has one or a plurality of needle-shaped distal end portions which project into a space outside the ceramic laminate and generate the gaseous discharge.

According to the particulate sensor (1), the ion source comprises a ceramic structure including a ceramic laminate, and a discharge electrode member which has an inter-layer portion and an exposed portion. The ion source generates a gaseous discharge between the reference potential member and the exposed portion when a constant DC discharge potential is applied thereto. The exposed portion of the discharge electrode member has a needle-shaped distal end portion which projects into the space outside the ceramic laminate without contacting the ceramic laminate and which generates the gaseous discharge.

As a result, an insulating ceramic layer serving as a dielectric is not present between the reference potential member and the needle-shaped distal end portion of the discharge electrode member (exposed portion), which projects into the space and generates the gaseous discharge. Therefore, it is possible to generate a gaseous discharge (corona discharge) by applying a constant DC discharge potential (which is not pulsed) to the discharge electrode member (needle-shaped distal end portion). Also, the control circuit configuration can be made simple and inexpensive, whereby the particulate sensor can be made inexpensively as well.

Notably, the shape of the ceramic structure; i.e., the shape of the ceramic laminate which constitutes the ceramic structure, is not limited to a plate-like shape, but may assume the shape of a quadrangular prism, a hexagonal prism, a circular column, or a circular tube. For example, in the case of a plate-shaped ceramic structure, a plurality of ceramic layers are layered in the thickness direction so as to form the ceramic laminate, and the inter-layer portion of the discharge electrode member is embedded between two of the ceramic layers of the ceramic laminate. In the case of a circular columnar ceramic structure, a ceramic laminate is formed by layering a plurality of ceramic layers to form annular rings similar to the annual rings of a tree, and a discharge electrode member is provided in the ceramic laminate in such a manner that the discharge electrode member is located between two of the ceramic layers and projects outward. In the case of the circular tubular ceramic structure, a ceramic laminate is formed by spirally winding one or a plurality of ceramic sheets in such a manner that a plurality of ceramic layers are layered in the radial direction. Also, a discharge electrode member is provided in the ceramic laminate in such a manner that the discharge electrode member is located between two of the ceramic layers and projects outward.

In a preferred embodiment (2) of the particulate sensor (1) above, the ceramic structure has a heater which is disposed within the ceramic laminate and heats the exposed portion of the discharge electrode member when energized.

The ceramic structure of the particulate sensor (2) has a heater for heating the exposed portion of the discharge electrode member. Therefore, foreign substances, such as water droplets and soot, adhering to the exposed portion of the discharge electrode member can be removed by heating the exposed portion. Consequently, insulation of the exposed portion which may have deteriorated can be recovered, and the ions can be properly generated by means of the gaseous discharge.

In another preferred embodiment (3), the particulate sensor (1) or (2) above further comprises a collection electrode which is maintained at a collection potential and collects floating ions which are some of the ions generated by the ion source that have not adhered to the particulates, wherein the ceramic structure has an auxiliary electrode portion which is maintained at an auxiliary potential and assists in collection of the floating ions by the collection electrode.

In the particulate sensor (3), a collection electrode is provided, and the ceramic structure has an auxiliary electrode portion provided separately from the discharge electrode member. Therefore, floating ions can be collected by the collection electrode more reliably.

In yet another preferred embodiment (4) of the particulate sensor (3) above, the reference potential member also serves as the collection electrode.

In the particulate sensor (4), the reference potential member is also used as the collection electrode (namely, the collection electrode and the reference potential electrode are at the same potential). As a result, the ion source can generate a gaseous discharge between the needle-shaped distal end portion of the discharge electrode member (exposed portion) and the reference potential member, and the reference potential member can collect the floating ions. Therefore, the ion source (ceramic structure) and the configuration therearound can be simplified.

In yet another preferred embodiment (5) of the particulate sensor (3) or (4) above, the ceramic laminate extends in a longitudinal direction; the auxiliary electrode portion is disposed within the ceramic laminate and is located on a forward end side of the ceramic laminate in the longitudinal direction; the exposed portion of the discharge electrode member is disposed within the ceramic laminate and is located on a rear end side of the ceramic laminate in the longitudinal direction; and when the particulate sensor is in use, the gas under measurement flows around a portion of the ceramic laminate, the portion extending from the exposed portion to the auxiliary electrode portion, from the rear end side toward the forward end side in the longitudinal direction.

In the particulate sensor (5), when the particulate sensor is in use, the gas under measurement flows around a portion of the ceramic laminate, the portion extending from the exposed portion to the auxiliary electrode portion, from the rear end side toward the forward end side. As a result, ions generated near the exposed portion flow, together with the gas under measurement, toward the auxiliary electrode portion located on the forward end side thereof. Accordingly, floating ions can be properly collected using the auxiliary electrode portion.

Notably, the auxiliary electrode portion may be provided on the surface of the ceramic laminate that is to be exposed. However, in the above-described particulate sensor, since the auxiliary electrode portion is provided within the ceramic laminate, lowering of the insulation resistance between the auxiliary electrode portion and the discharge electrode member, etc., due to adhesion of water and/or soot is prevented.

In yet another preferred embodiment (6) of the particulate sensor (5) above, the ceramic laminate includes a first ceramic portion extending in the longitudinal direction and composed of a plurality of ceramic layers; and a second ceramic portion layered on the first ceramic portion, composed of one or a plurality of ceramic layers, and being shorter than the first ceramic portion in the longitudinal direction. A second forward end of the second ceramic portion which is an end of the second ceramic portion located on the forward end side in the longitudinal direction is offset toward the rear end side in the longitudinal direction from a first forward end of the first ceramic portion which is an end of the first ceramic portion located on the forward end side in the longitudinal direction. The exposed portion of the discharge electrode member projects from the second forward end of the second ceramic portion; and the auxiliary electrode portion is provided in the first ceramic portion and is located on the forward end side in the longitudinal direction in relation to the second forward end of the second ceramic portion.

In the particulate sensor (6), the exposed portion of the discharge electrode member projects from the second forward end of the second ceramic portion, which is offset toward the rear end side in the longitudinal direction from the first forward end of the first ceramic portion. Also, the auxiliary electrode portion is provided in the first ceramic portion and is located on the forward end side in the longitudinal direction in relation to the second forward end of the second ceramic portion. As a result, gaseous discharge can be reliably generated using a simple configuration, and floating ions can be properly collected using the auxiliary electrode portion.

In yet another preferred embodiment (7) of the particulate sensor (1) or (2) above, the ceramic laminate has a plate-like shape and has two main faces; and the exposed portion of the discharge electrode member projects from an end surface of the ceramic laminate which connects the main faces of the ceramic laminate.

In the particulate sensor (7), since the exposed portion of the discharge electrode member projects from the end surface of the plate-shaped ceramic laminate, gaseous discharge can be reliably generated between the exposed portion and the reference potential member using a simple configuration.

In yet another preferred embodiment (8) of the particulate sensor of any of (1) to (7) above, the ceramic structure is formed by integral firing of its constituent members.

In the particulate sensor (8), since the ceramic structure is formed by integral firing, it is possible to manufacture a ceramic element in which the discharge electrode member and the ceramic substrate are reliably integrated.

DESCRIPTION OF SYMBOLS AND REFERENCE NUMERALS

Figure 1:
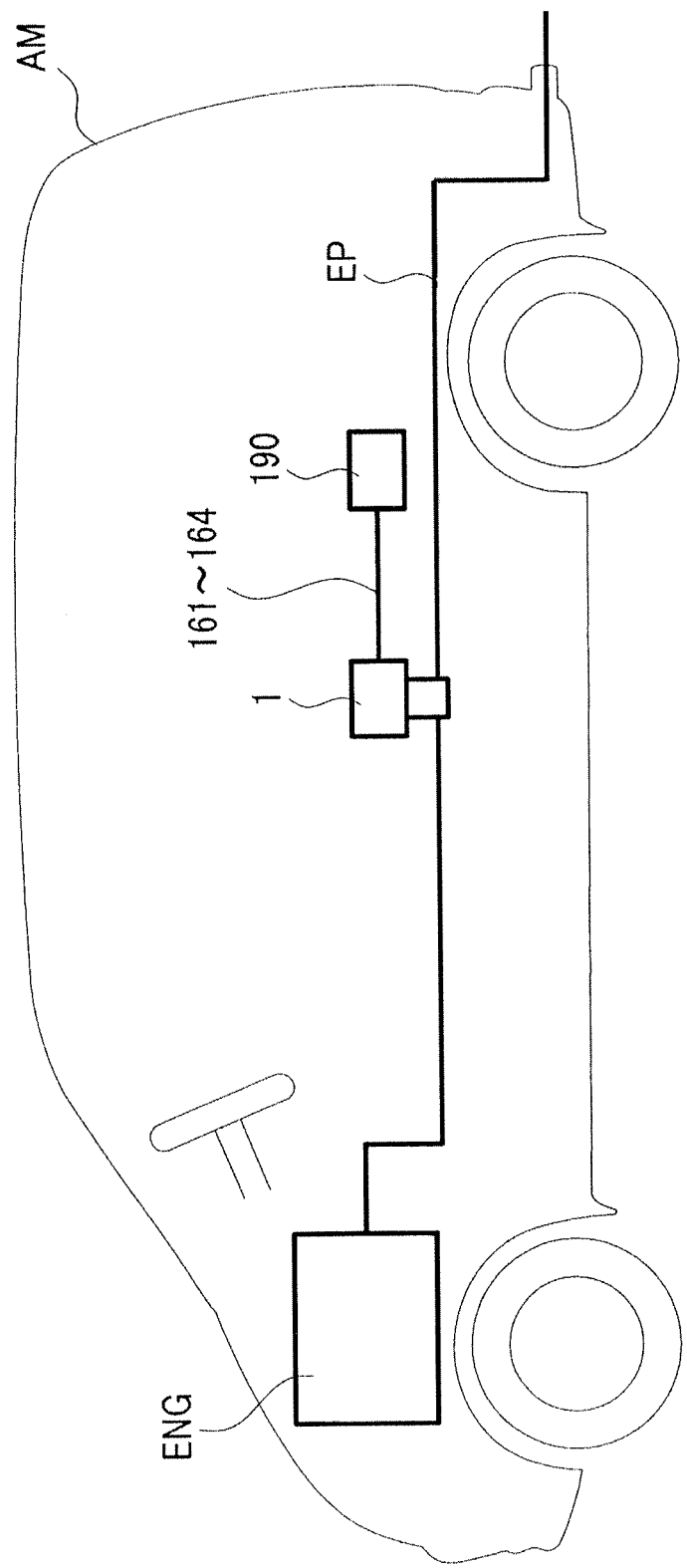
FIG. 1 is an explanatory view relating to an embodiment and showing a state in which a particulate sensor is applied to an exhaust pipe of an engine mounted on a vehicle.

Symbols and reference numbers used to identify various features in the drawings include the following.
EP: exhaust pipe
EG: exhaust gas (gas under measurement)
CGND: chassis GND potential
SGND: sensor GND potential
PV2: discharge potential
PV3: auxiliary potential
S: particulate
CP: ion
CPF: floating ion
GS: forward end side
GK: rear end side
HN: longitudinal direction
1, 1A: particulate sensor
15: ion source
40: outer protector
45: inner protector (reference potential member, collection electrode)
50: metallic shell
71: first separator
72: second separator
73: discharge potential terminal
75: auxiliary potential terminal
76: first heater terminal
77: second heater terminal
80: inner tube
90: mounting metallic member
95: outer tube
100, 100A: ceramic element (ceramic structure)
101: ceramic substrate (ceramic laminate)
101A: first ceramic portion
101AS: first forward end portion
101B: second ceramic portion
101BS: second forward end portion
101S1, 101S2: main face
101S: end surface
102, 103, 104: ceramic layer
105, 106: insulating cover layer
110: discharge electrode member
111: lead portion (inter-layer portion)
112: needle-shaped electrode portion
112A: embedment portion (inter-layer portion)
112B: exposed portion
112S: needle-shaped distal end portion
120: auxiliary electrode member
122: auxiliary electrode portion
130: heater
131: heat generation portion
161: discharge potential lead wire
162: auxiliary potential lead wire
163: first heater lead wire
164: second heater lead wire

DETAILED DESCRIPTION OF THE PREFERRED EMBODIMENTS

The present invention will next be described in detail with reference to the drawings. However, the present invention should not be construed as being limited thereto.

Embodiment:

As shown in FIG. 1, the particulate sensor 1 of the present embodiment is attached to an exhaust pipe EP of an engine ENG mounted on a vehicle AM, and detects particulates S (soot, etc.) contained in exhaust gas EG (gas under measurement) flowing through the exhaust pipe EP.

First, the mechanical structure of the particulate sensor 1 will be described with reference to a longitudinal sectional view of FIG. 2 and an exploded perspective view of FIG. 3. Notably, in FIG. 2, the lower side corresponds to the forward end side GS of the particulate sensor 1 in the longitudinal direction HN, and the upper side corresponds to the rear end side GK of the particulate sensor 1. Also, in FIG. 3, the closer to the lower side and the right side, the closer to the forward end side GS of the particulate sensor 1.

The particulate sensor 1 includes a plate-shaped ceramic element 100 which extends in the longitudinal direction HN and generates ions by gaseous discharge. In addition, the particulate sensor 1 includes a metallic shell 50 which holds the ceramic element 100 in an insulated state and which is maintained at a sensor GND potential SGND; members joined to the metallic shell 50; a mounting metallic member 90 which is insulated from the metallic shell 50, etc., which surrounds and holds these members, and which is attached to the exhaust pipe EP to thereby be maintained at a chassis GND potential CGND; members joined to the mounting metallic member 90; etc.

Specifically, the tubular mounting metallic member 90 is provided on the forward end side GS of the particulate sensor 1. The mounting metallic member 90 has a flange portion 91 which projects radially outward so as to form a hexagonal outer shape. A male screw used for attachment to the exhaust pipe EP is formed on the outer circumference of a forward end portion 90s of the mounting metallic member 90 which is located on the forward end side GS in relation to the flange portion 91. By means of the male screw of the forward end portion 90s of the mounting metallic member 90, the particulate sensor 1 is attached to an attachment boss BO which is formed of metal and is separately fixed to the exhaust pipe EP, whereby the particulate sensor 1 is fixed to the exhaust pipe EP via the attachment boss BO. Therefore, the mounting metallic member 90 is maintained at the chassis GND potential CGND, which is the same as the potential of the exhaust pipe EP.

An outer tube 95 formed of metal is fixed to an end of the mounting metallic member 90 on the rear end side GK. Specifically, a forward end portion 95s of the outer tube 95 is fitted onto a rear end portion 90k of the mounting metallic member 90, and is integrated therewith by means of laser welding.

The tubular metallic shell 50 and an inner tube 80 integrated therewith are disposed on the radially inner side of the mounting metallic member 90 with first and second insulating spacers 60 and 61 (formed of an insulating material) interposed therebetween. Also, together with these members, a tubular sleeve 62 and an annular line packing 63 are disposed within the mounting metallic member 90.

Specifically, the metallic shell 50 has an annular flange 51 projecting radially outward, and a forward end portion of the inner tube 80 is formed into an annular flange 81. The forward end portion 80s of the inner tube 80 is fitted onto a rear end portion 50k of the metallic shell 50 so that the flanges 51 and 81 overlie each other, and is connected to the rear end portion 50k by means of laser welding. The metallic shell 50 and the inner tube 80 connected together are disposed within the mounting metallic member 90 in such a manner that the flanges 51 and 81 are sandwiched between the first insulating spacer 60 located on the forward end side GS and the second insulating spacer 61 located on the rear end side GK. Further, the sleeve 62 is disposed on the rear end side GK of the second insulating spacer 61. The line packing 63 is disposed between the sleeve 62 and a rearmost end portion 90kk of the mounting metallic member 90, and the rearmost end portion 90kk of the mounting metallic member 90 is bent radially inward by crimping.

A metal cup 52 is disposed within the metallic shell 50. The plate-shaped ceramic element 100 serving as an ion source 15 extends through a hole formed in the bottom wall of the metal cup 52. Around the ceramic element 100, a tubular ceramic holder 53 formed of alumina and holding the ceramic element 100, first and second powder charged layers 54 and 55 formed by compressing a talc powder, and a tubular ceramic sleeve 56 formed of alumina are disposed in this order from the forward end side GS toward the rear end side GK. Notably, of these, the ceramic holder 53 and the first powder charged layer 54 are located within the metal cup 52.

Further, a crimp ring 57 is disposed between the rearmost end portion 50kk of the metallic shell 50 and the ceramic sleeve 56, and the rearmost end portion 50kk of the metallic shell 50 is bent radially inward by crimping, to thereby press the ceramic sleeve 56 through the crimp ring 57. As a result, the powder of the second powder charged layer 55 is compressed, whereby the metal cup 52 and the ceramic sleeve 56 are fixed within the metallic shell 50, and the ceramic element 100 is gastightly held by the metallic shell 50.

A double-wall tubular protector composed of an inner protector 45 and an outer protector 40 formed of stainless steel is fixedly provided at a forward end portion 50s of the metallic shell 50, and surrounds a forward end portion of the ceramic element 100 from the radially outer side. The tubular protector protects the ceramic element 100 from water droplets and foreign substances, and introduces the exhaust gas EG into a space around the ceramic element 100. The inner protector 45 and the outer protector 40 are fixed to the forward end portion 50s as follows. A large diameter portion 47 of the inner protector 45 on the rear end side GK is fitted onto the forward end portion 50s of the metallic shell 50, a large diameter portion 42 of the outer protector 40 on the rear end side GK is fitted onto the large diameter portion 47, and the large diameter portions 42 and 47 are fixed to the forward end portion 50s of the metallic shell 50 by means of laser welding.

A plurality of rectangular outer introduction holes 40I for introducing the exhaust gas EG are formed in a tubular trunk portion 41 of the outer protector 40 and are located in a circumferential region on the forward end side GS. Also, a plurality of triangular inner introduction holes 45I and a plurality of circular inner introduction holes 45I are formed in a tubular trunk portion 46 of the inner protector 45 in such a manner that the triangular inner introduction holes 45I are located in a circumferential region on the forward end side GS and the circular inner introduction holes 45I are located in a circumferential region on the rear end side GK.

Further, a circular discharge opening 45O for discharging the introduced exhaust gas EG (gas under measurement) is formed in a forward end portion of the inner protector 45. The forward end portion of the inner protector 45, including the discharge opening 45O, projects outward from an opening 43 of a forward end portion of the outer protector 40.

Here, with reference to FIG. 6, the action of the inner protector 45 and the outer protector 40 will be described; i.e., the introduction and discharge of the exhaust gas EG into and from the interiors of the inner protector 45 and the outer protector 40 at the time when the particulate sensor 1 is in use.

Figure 6:
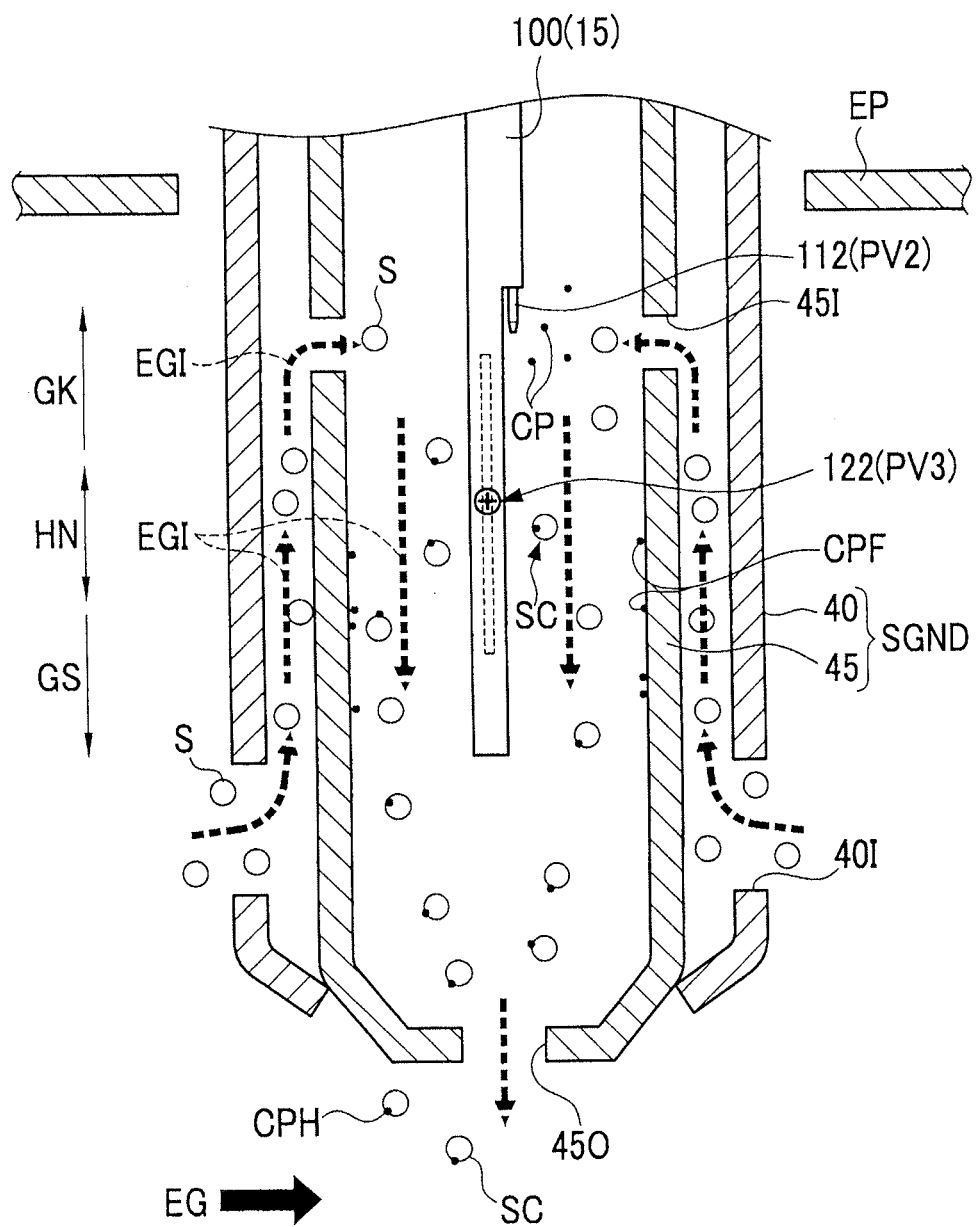
FIG. 6 is an explanatory view schematically showing the electrical function and operation of the particulate sensor according to the embodiment, as well as introduction and discharge of exhaust gas.

In FIG. 6, the exhaust gas EG flows within the exhaust pipe EP from the left-hand side toward the right-hand side. When the exhaust gas EG flowing within the exhaust pipe EP passes through a region around the outer protector 40 and the inner protector 45 of the particulate sensor 1, its flow velocity increases on the outer side of the discharge opening 45O of the inner protector 45, and a negative pressure is produced near the discharge opening 45O due to the so-called Venturi effect. On account of this negative pressure, the exhaust gas EGI introduced into the inner protector 45 is discharged through the discharge opening 45O. Simultaneously, the exhaust gas EG around the outer introduction holes 40I of the outer protector 40 is introduced into the interior of the outer protector 40 through the outer introduction holes 40I, and is further introduced into the interior of the inner protector 45 through the inner introduction holes 45I of the inner protector 45.

Since the introduced exhaust gas EGI within the inner protector 45 is discharged through the discharge opening 45O, a flow of the introduced exhaust gas EGI from the inner introduction holes 45I on the rear end side GK toward the discharge opening 45O on the forward end side GS is produced within the inner protector 45.

Figure 2:
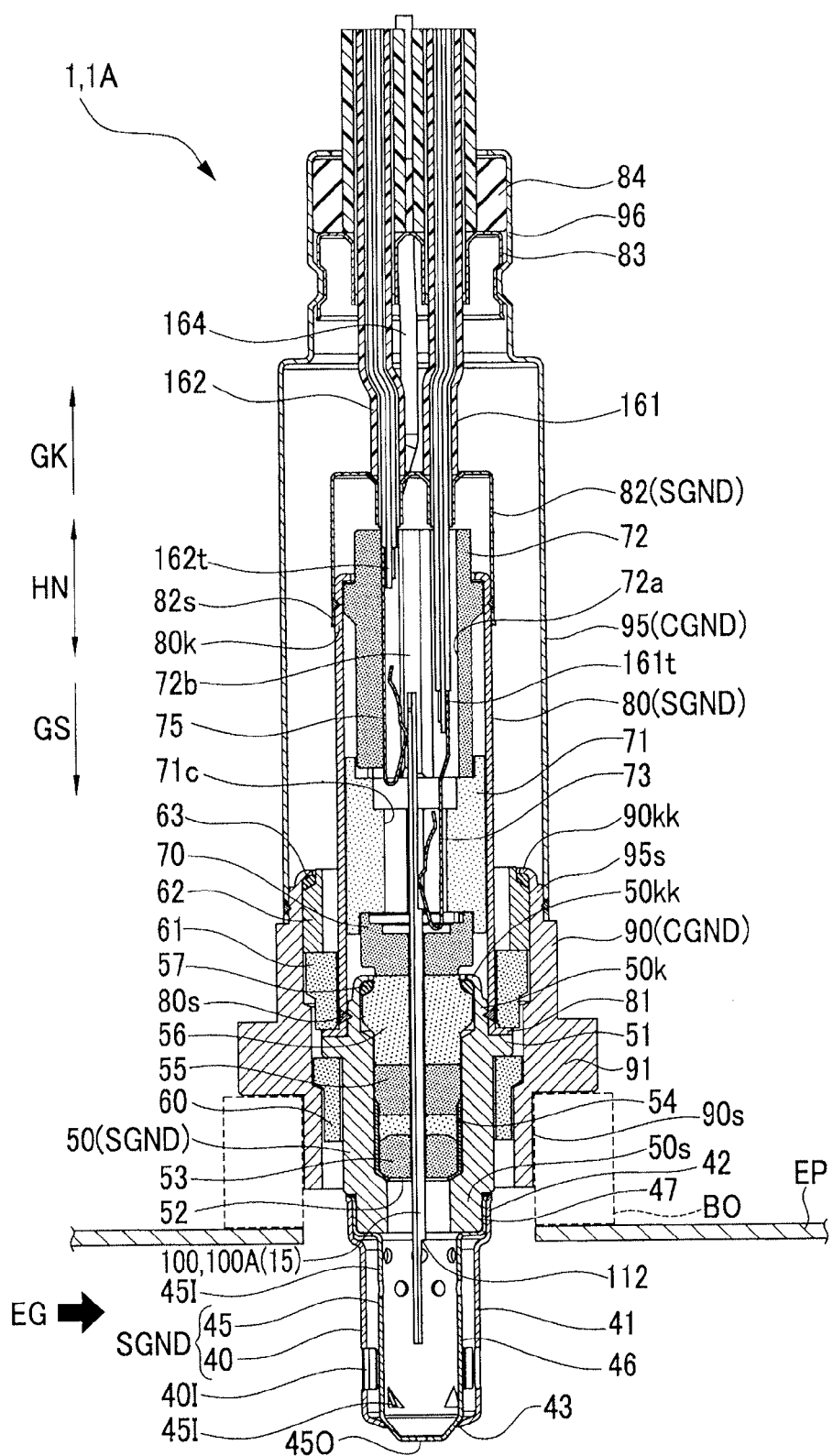
FIG. 2 is a longitudinal sectional view of the particulate sensor according to the embodiment.
Figure 3:
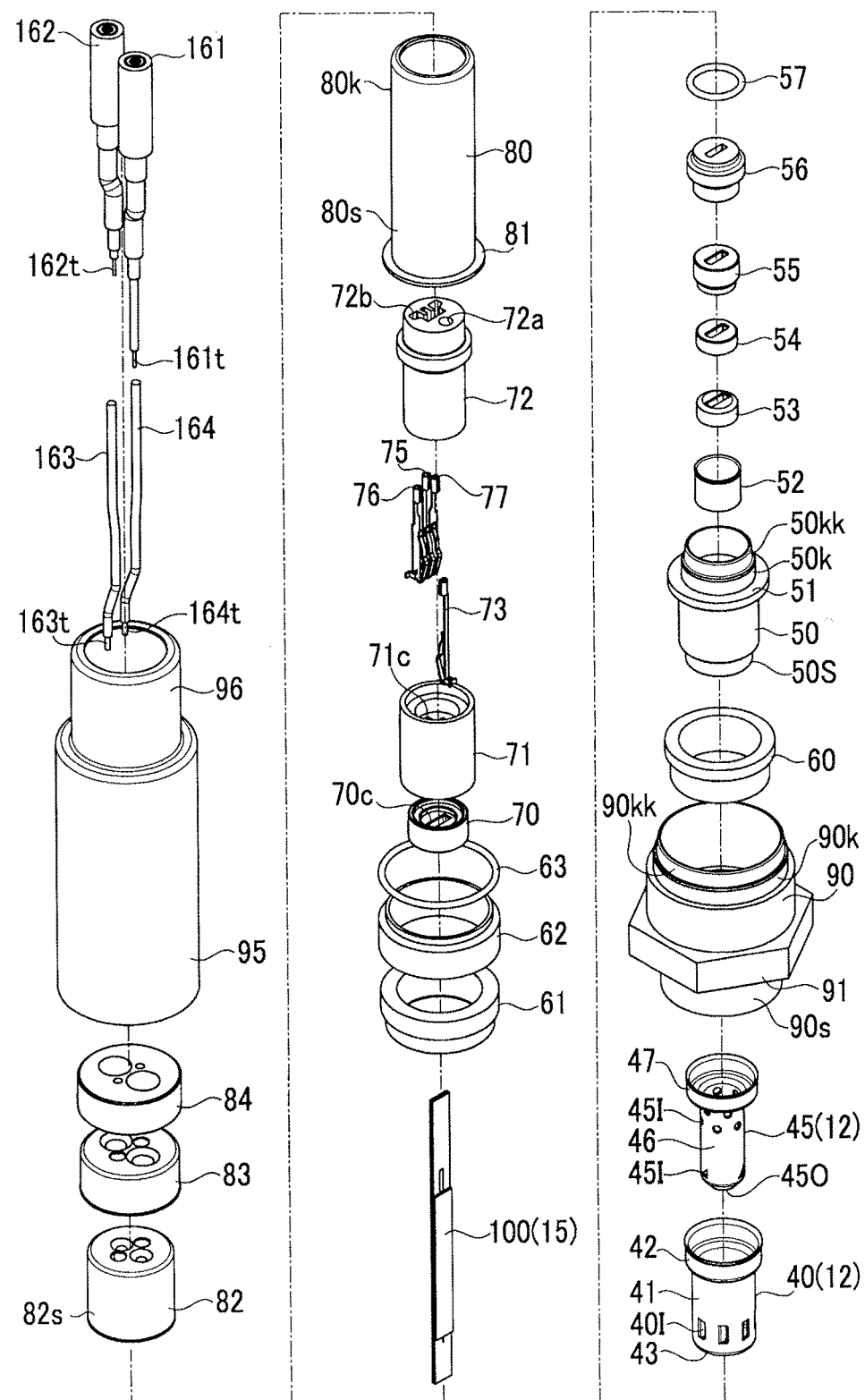
FIG. 3 is an exploded perspective view showing the structure of the particulate sensor according to the embodiment.

Next, resuming the description of the mechanical structure of the particulate sensor 1 made with reference to FIGS. 2 and 3, an insulating holder 70 formed of an insulating material is disposed on the rear end side GK of the metallic shell 50; i.e., on the outer side (toward the rear end side GK) of the ceramic sleeve 56 located within the metallic shell 50, and is located within the inner tube 80. The ceramic element 100 is inserted into an insertion hole 70c of the insulating holder 70.

Also, a first separator 71 formed of an insulating material is disposed on the rear end side GK of the insulating holder 70, and a second separator 72 formed of an insulating material is disposed on the rear end side GK of the first separator 71. Thus, the first and second separators 71 and 72 are arranged in tandem in the longitudinal direction HN, and are accommodated within the inner tube 80.

The first separator 71 has an insertion hole 71c. The ceramic element 100 extends through the insertion hole 71c, and a discharge potential terminal 73 is accommodated in the insertion hole 71c. The second separator 72 has a first insertion hole 72a and a second insertion hole 72b. A rear end portion 100K (see FIG. 4) of the ceramic element 100 is located in the second insertion hole 72b, and an auxiliary potential terminal 75, a first heater terminal 76, and a second heater terminal 77 are accommodated in the second insertion hole 72b.

Notably, within the insertion hole 71c of the first separator 71, the discharge potential terminal 73 is in contact with a discharge potential pad 113 (described below) of the ceramic element 100 (see FIGS. 4 and 5). Within the second insertion hole 72b of the second separator 72, the auxiliary potential terminal 75 is in contact with an auxiliary potential pad 125 of the ceramic element 100, the first heater terminal 76 is in contact with a first heater pad 136 of the ceramic element 100, and the second heater terminal 77 is in contact with a second heater pad 137 of the ceramic element 100.

Further, within the first insertion hole 72a of the second separator 72, the discharge potential terminal 73 is connected to an end portion 161t of a discharge potential lead wire 161. Also, within the second insertion hole 72b of the second separator 72, the auxiliary potential terminal 75 is connected to an end portion 162t of an auxiliary potential lead wire 162, the first heater terminal 76 is connected to an end portion 163t of a first heat lead wire 163, and the second heater terminal 77 is connected to an end portion 164t of a second heat lead wire 164.

A forward end portion 82s of a sensor GND metal connection member 82 is fitted onto a rear end portion 80k of the inner tube 80, and is laser-welded thereto. The discharge potential lead wire 161, the auxiliary potential lead wire 162, the first heat lead wire 163, and the second heat lead wire 164 are passed through the sensor GND metal connection member 82. Of these wires, the discharge potential lead wire 161 and the auxiliary potential lead wire 162 are the core wires (center conductors) of triple coaxial cables (triaxial cables). Of the coaxial double outer conductors of each cable, the outer conductor located on the inner side is maintained at a sensor GND potential SGND, which is a reference potential for the sensor, and is in electrical contact with the sensor GND metal connection member 82. As a result, all of the inner tube 80, the metallic shell 50, the inner protector 45, the outer protector 40, which are in electrical contact with the sensor GND metal connection member 82, are maintained at the sensor GND potential SGND.

Further, a grommet 84 formed of fluororubber and a chassis GND metal connection member 83 are disposed within a small diameter portion 96 of the outer tube 95 located on the rear end side GK. The discharge potential lead wire 161, the auxiliary potential lead wire 162, the first heat lead wire 163, and the second heat lead wire 164 are passed through the grommet 84 and the chassis GND metal connection member 83. Of the coaxial double outer conductors of the triple coaxial cables whose core wires are the discharge potential lead wire 161 and the auxiliary potential lead wire 162, the outer conductors located on the outer side are in electrical contact with the chassis GND metal connection member 83. The chassis GND metal connection member 83 is crimped together with the small diameter portion 96 of the outer tube 95 so that the diameter of the chassis GND metal connection member 83 decreases. Thus, the grommet 84 and the chassis GND metal connection member 83 are fixed within the small diameter portion 96 of the outer tube 95. As a result, all of the mounting metallic member 90, the outer tube 95, the chassis GND metal connection member 83, which are in electrical contact with the exhaust pipe EP and the attachment boss BO, are maintained at the chassis GND potential CGND. Notably, the chassis GND potential CGND is the same as the GND potential of a battery (not shown) mounted on the vehicle AM.

Next, the structure of the ceramic element 100 will be described in detail. As shown in FIGS. 4 and 5, the ceramic element 100 has a plate-shaped insulative ceramic substrate 101 formed of alumina. A discharge electrode member 110, an auxiliary electrode member 120, and a heater 130 are embedded in the ceramic substrate 101, and are integrated by firing (integral firing).

More specifically, the ceramic substrate 101 is a ceramic laminate in which three plate-shaped ceramic layers 102, 103, and 104 formed of alumina originating from an alumina green sheet are layered together. More specifically, two insulating cover layers 105 and 106 of alumina are formed between these layers by printing. As shown in FIG. 5, the ceramic layer 102, the insulating cover layer 105, the ceramic layer 103, the insulating cover layer 106, and the ceramic layer 104 are layered in this order. The discharge electrode member 110 is disposed between the ceramic layer 102 and the ceramic layer 103; more specifically, between the insulating cover layer 105 and the ceramic layer 103. The auxiliary electrode member 120 is disposed between the ceramic layer 103 and the ceramic layer 104; more specifically, between the ceramic layer 103 and the insulating cover layer 106. The heater 130 is disposed between the insulating cover layer 106 and the ceramic layer 104. The layers, the members, and the heater are integrated, whereby the ceramic element 100 (ceramic structure) is formed.

Figure 4:
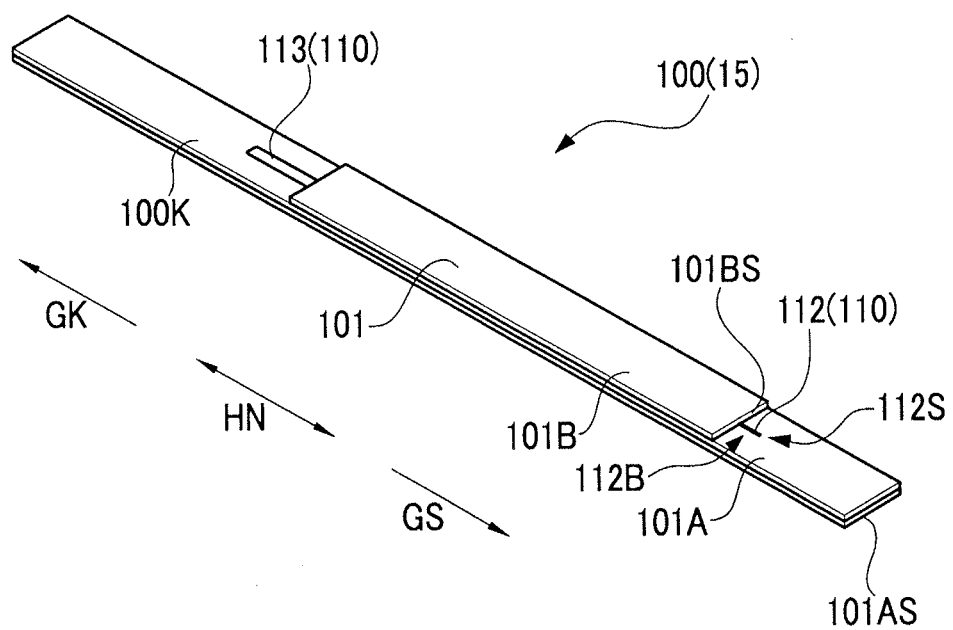
FIG. 4 is a perspective view showing the entirety of a ceramic element of the particulate sensor according to the embodiment.

Notably, in the present embodiment, as shown in FIG. 4, the ceramic substrate 101 (ceramic laminate) of the ceramic element 100 has a structure in which a second ceramic portion 101B composed of the ceramic layer 102 and shorter than the ceramic layers 103 and 104 as measured in the longitudinal direction HN is layered on a first ceramic portion 101A composed of the ceramic layers 103 and 104. A second forward end 101BS of the second ceramic portion 101B located on the forward end side GS in the longitudinal direction HN is offset or shifted toward the rear end side GK in the longitudinal direction HN from a first forward end 101AS of the first ceramic portion 101A located on the forward end side GS in the longitudinal direction HN.

In the ceramic element 100, the discharge electrode member 110 extends in the longitudinal direction HN, and has a needle-shaped electrode portion 112 formed of platinum wire, a lead portion 111 in electrical contact with the needle-shaped electrode portion 112 and formed on one surface 103S1 of the ceramic layer 103 by pattern printing, and a discharge potential pad 113 in electrical contact with the lead portion 111.

The lead portion 111 of the discharge electrode member 110 and an embedment portion 112A (on the rear end side GK) of the needle-shaped electrode portion 112 connected to the lead portion 111 are inter-layer portions which are covered by the insulating cover layer 105 and the ceramic layer 102 and are embedded in the ceramic substrate 101 (ceramic laminate); specifically, between the ceramic layer 102 and the ceramic layer 103.

Since the inter-layer portions (the embedment portion 112A and the lead portion 111) are embedded in the ceramic substrate 101, it is possible to prevent the insulating property of the inter-layer portions 112A and 111 from deteriorating due to water or soot adhering to the ceramic substrate 101. In addition, since the inter-layer portions 112A and 111 are formed between the ceramic layer 102 and the ceramic layer 103, the inter-layer portions 112A and 111 can be easily formed by pattern printing or by disposing platinum wire.

Meanwhile, an exposed portion 112B (on the forward end side GS) of the needle-shaped electrode portion 112 formed of platinum wire projects from the second forward end 101BS of the second ceramic portion 101B of the ceramic substrate 101. In addition, a needle-shaped distal end portion 112S of the exposed portion 112B located on the forward end side GS and having a tapered shape is bent so that the end of the needle-shaped distal end portion 112S is separated from the surface 103S1 of the ceramic layer 103 by 2 to 3 mm; i.e., the needle-shaped distal end portion 112S projects into the space outside the ceramic substrate 101 while being separated from the surface 103S1 of the ceramic layer 103.

The discharge potential pad 113 is not covered by the insulating cover layer 105 and the ceramic layer 102, and is exposed on the surface 103S1 of the ceramic layer 103 of the ceramic substrate 101 at a position on the rear end side GK. As described above, the discharge potential terminal 73 is in physical and electrical contact with the discharge potential pad 113.

The auxiliary electrode member 120 has a rectangular auxiliary electrode portion 122 formed by means of pattern printing and disposed on the forward end side GS of the ceramic element 100, and an auxiliary electrode lead portion 121 in electrical contact with the auxiliary electrode portion 122 and extending toward the rear end side GK of the ceramic element 100. The auxiliary electrode member 120 is formed on a surface 103S2 of the ceramic layer 103 opposite the surface 103S1, and is covered by the insulating cover layer 106. Thus, the auxiliary electrode member 120 is embedded in the ceramic substrate 101; specifically, between the ceramic layer 103 and the ceramic layer 104.

Notably, the auxiliary electrode portion 122 of the auxiliary electrode member 120 is embedded in the first ceramic portion 101A of the ceramic substrate 101 (between the ceramic layer 103 and the ceramic layer 104) and located on the forward end side GS in the longitudinal direction HN in relation to the second forward end 101BS of the second ceramic portion 101B.

Meanwhile, the auxiliary electrode lead portion 121 of the auxiliary electrode member 120 has an end portion 123 on the rear end side GK. The end portion 123 is in electrical contact with a conductor pattern 124 formed on one surface 104S1 of the ceramic layer 104 by means of a through hole 106c of the insulating cover layer 106. The conductor pattern 124 is in electrical contact with an auxiliary potential pad 125 formed on the other surface 104S2 of the ceramic layer 104 by means of a through hole 104h1 extending through the ceramic layer 104. Notably, as described above, the auxiliary potential terminal 75 is in physical and electrical contact with the auxiliary potential pad 125.

Also, the heater 130 is formed on the one surface 104S1 of the ceramic layer 104 by pattern printing. The heater 130 has a heat generation portion 131 which is disposed on the forward end side GS of the ceramic element 100 and heats the exposed portion 112B of the needle-shaped electrode portion 112 of the discharge electrode member 110 when energized. Also, two heater lead portions 132 and 133 are in electrical contact with the heat generation portion 131 and extend toward the rear end side GK of the ceramic element 100. The heater 130 is formed on the one surface 104S1 of the ceramic layer 104, and is covered by the insulating cover layer 106.

The heater lead portions 132 and 133 of the heater 130 have end portions 134 and 135 on the rear end side GK. The end portions 134 and 135 are in electrical contact, by means of through holes 104h2 extending through the ceramic layer 104, with a first heater pad 136 and a second heater pad 137, respectively, which are formed on the other surface 104S2 of the ceramic layer 104. Notably, as described above, the first heater terminal 76 is in electrical contact with the first heater pad 136, and the second heater terminal 77 is in contact with the second heater pad 137.

Next, the detection of particulates using the particulate sensor 1 of the present embodiment will be described.

Of members constituting the ceramic element 100 serving as the ion source 15, the discharge electrode member 110, the auxiliary electrode member 120 and the heater 130 are connected to a circuit section 190 not shown in FIG. 2 (see FIG. 1) through the above-described discharge potential lead wire 161, the auxiliary potential lead wire 162, the first heat lead wire 163 and the second heat lead wire 164. Also, of the coaxial double outer conductors of the above-described triple coaxial cables (triaxial cables) whose core wires serve as the discharge potential lead wire 161 and the auxiliary potential lead wire 162, the outer conductors located on the inner side are also connected to the circuit section 190. The inner protector 45 disposed around the ceramic element 100 (ion source 15) is maintained at the sensor GND potential SGND (reference potential) as described above.

Figure 5:
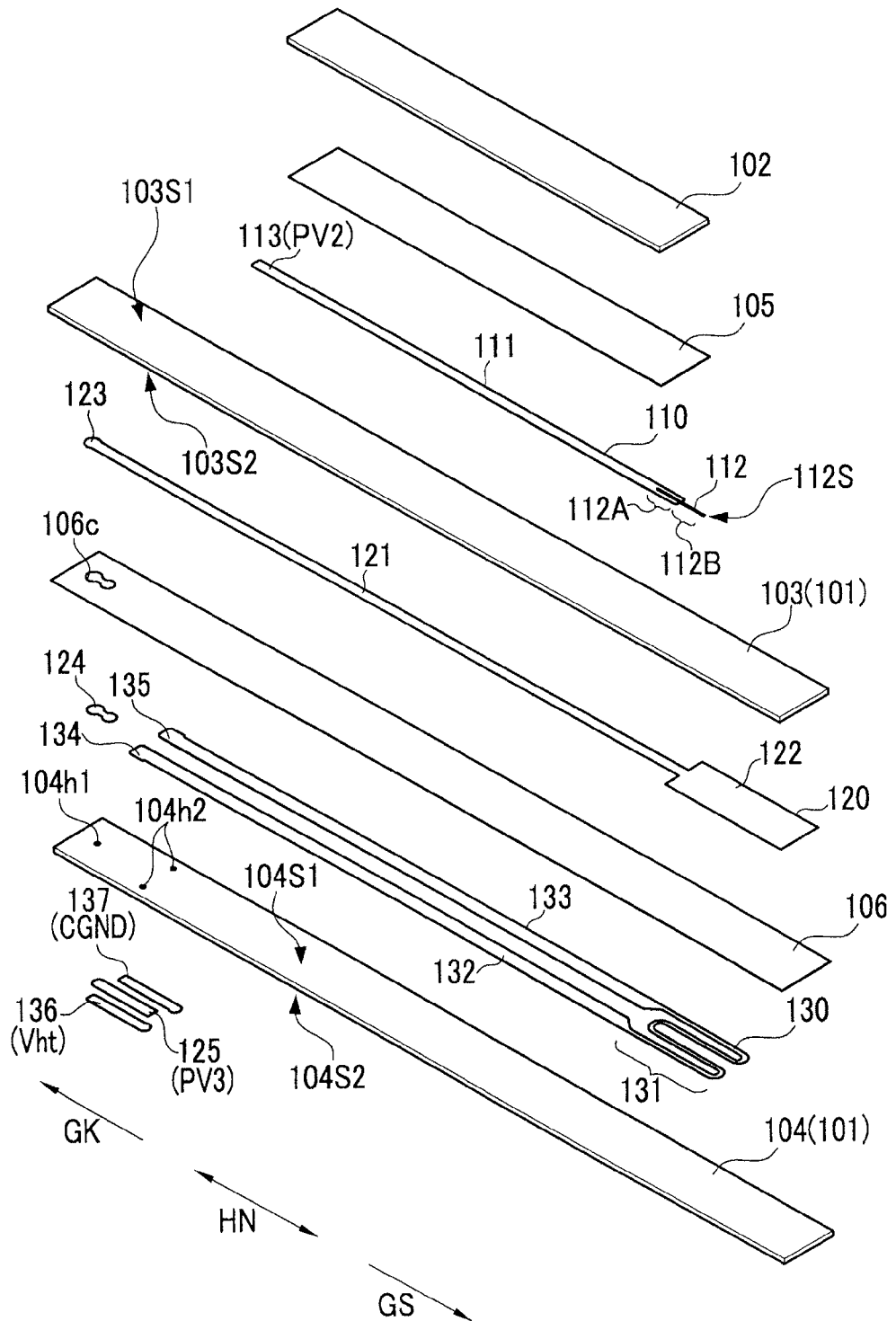
FIG. 5 is an exploded perspective view showing the structure of the ceramic element of the particulate sensor according to the embodiment.

A DC high voltage (e.g., 1 to 2 kV) is supplied from the circuit section 190 to the needle-shaped electrode portion 112 of the discharge electrode member 110 through the discharge potential terminal 73 and the discharge potential pad 113 so that the needle-shaped electrode portion 112 is maintained at a predetermined discharge potential PV2 (see FIG. 5). As a result, a gaseous discharge; specifically, a corona discharge, occurs between the needle-shaped distal end portion 112S of the exposed portion 112B of the needle-shaped electrode portion 112 and the inner protector 45 (reference potential member) maintained at the sensor GND potential SGND (reference potential), whereby ions CP (see FIG. 6) are generated around the needle-shaped distal end portion 112S. As described above, by action of the outer protector 40 and the inner protector 45, the exhaust gas EG is introduced into the interior of the inner protector 45, and a flow of the introduced exhaust gas EGI from the rear end side GK toward the forward end side GS is produced near the ceramic element 100. As shown in FIG. 6, the generated ions CP adhere to particulates S contained in the introduced exhaust gas EGI. As a result, the particulates S become positively charged particulates SC, which flow toward the discharge opening 45O together with the introduced exhaust gas EGI, and are discharged.

Meanwhile, a predetermined voltage (e.g., a positive DC voltage of 100 to 200 V) is applied from the circuit section 190 to the auxiliary electrode portion 122 of the auxiliary electrode member 120 through the auxiliary potential terminal 75 and the auxiliary potential pad 125 so that the auxiliary electrode portion 122 is maintained at a predetermined auxiliary potential PV3 (see FIG. 5). Thus, a repulsive force directed from the auxiliary electrode portion 122 toward the inner protector 45 (collection electrode) located on the radially outer side acts on floating ions CPF (see FIG. 6), which are some of the ions CP generated by the ion source 15 that have not adhered to the particulates S. As a result, the floating ions CPF adhere to various portions of the collection electrode (inner protector 45), whereby collection of the floating ions CPF by the collection electrode is assisted. Thus, the floating ions CPF can be reliably collected, and are prevented from being discharged through the discharge opening 45O. In the particulate sensor 1, a signal (signal current) is detected corresponding to the amount of charge of discharged ions CPH which are discharged through the discharge opening 45O while adhering to the particulates S (the discharged ions CPH that are ions discharged in the form of the charged particulates SC). As a result, the amount (concentration) of the particulates S contained in the exhaust gas EG can be properly detected.

Notably, as described above, in the present embodiment, the inner protector 45 around the ceramic element 100 (ion source 15) is maintained at the sensor GND potential SGND (reference potential), and a corona discharge is generated between the needle-shaped distal end portion 112S and the inner protector 45. Additionally, the inner protector 45 serves as a collection electrode as well. Namely, in the present embodiment, the collection potential for collection by the inner protector 45 (collection electrode) is equal to the sensor GND potential SGND (reference potential).

Also, a predetermined heater energization voltage output from the circuit section 190 is applied between the first heater pad 136 and the second heater pad 137 through the first heater terminal 76 and the second heater terminal 77. As a result, the heat generation portion 131 of the heater 130 generates heat upon energization. This heats the exposed portion 112B of the needle-shaped electrode portion 112 projecting from the ceramic element 100, to thereby remove foreign substances, such as water droplets and soot, adhering to the exposed portion 112B of the needle-shaped electrode portion 112 and to portions around the exposed portion 112B. Thus, a deteriorated insulation property of the exposed portion 112B can be recovered.

Specifically, a voltage obtained through pulse control of the DC battery voltage (DC 12 V or 24 V) of the vehicle AM is applied as the heater energization voltage. For example, a first heater potential Vht applied to the first heater pad 136 through the first heater terminal 76 is a positive-side potential produced as a result of the pulse control of the battery voltage (DC 12 V or 24 V), and a second heater potential supplied to the second heater pad 137 through the second heater terminal 77 is the chassis GND potential CGND, which is the same as the GND potential of the battery (see FIG. 5).

As described above, in the particulate sensor 1 of the present embodiment, the ion source 15 includes the ceramic element 100 (ceramic structure) including the ceramic substrate 101 (ceramic laminate) and the discharge electrode member 110 which generates a corona discharge (gaseous discharge) upon application of the constant DC discharge potential PV2 thereto. The exposed portion 112B of the needle-shaped electrode portion 112 of the discharge electrode member 110 includes the tapered, needle-shaped distal end portion 112S which projects into the space outside the ceramic substrate 101 (ceramic laminate) without contacting the ceramic substrate 101 and which generates the corona discharge.

As a result, an insulating ceramic layer serving as a dielectric is not present between the inner protector 45 (reference potential member) maintained at the sensor GND potential (reference potential) and the needle-shaped distal end portion 112S of the exposed portion 112B of the needle-shaped electrode portion 112, which projects into the space. Therefore, it is possible to generate a corona discharge by applying the constant DC discharge potential PV2 to the needle-shaped distal end portion 112S of the discharge electrode member 110. As a result, the configuration of the circuit section 190 can be made simple and inexpensive, whereby the particulate sensor 1 can be made inexpensive as well.

Further, the heater 130 of the ceramic element 100 of the particulate sensor 1 of the present embodiment heats the exposed portion 112B of the needle-shaped electrode portion 112 of the discharge electrode member 110. Accordingly, foreign substances, such as water droplets and soot, adhering to the exposed portion 112B of the discharge electrode member 110, can be removed by heating the exposed portion 112B with the heat generation portion 131 of the heater 130. Consequently, a deteriorated insulation property of the exposed portion 112B can be recovered, and the ions CP can be properly generated by means of the corona discharge.

Further, the particulate sensor 1 of the present embodiment has a collection electrode (inner protector 45), and the ceramic element 100 (ceramic structure) includes the auxiliary electrode member 120 having the auxiliary electrode portion 122. This configuration allows the floating ions CPF to be reliably collected by the collection electrode (inner protector 45).

Further, in the particulate sensor 1 of the present embodiment, the inner protector 45 used as a reference potential member also serves as a collection electrode, and the collection potential is equal to the sensor GND potential SGND (reference potential). As a result, the ion source 15 (ceramic element 100) can generate a corona discharge (gaseous discharge) between the needle-shaped distal end portion 112S of the exposed portion 112B of the discharge electrode member 110 and the inner protector 45 (reference potential member), which also functions as a collection electrode. Therefore, the ion source 15 (ceramic element 100) and the configuration therearound can be simplified.

Further, in the particulate sensor 1 of the present embodiment, the exposed portion 112B of the discharge electrode member 110 projects from the second forward end 101BS of the second ceramic portion 101B. Also, the auxiliary electrode portion 122 of the auxiliary electrode member 120 is provided in the first ceramic portion 101A (between the ceramic layer 103 and the ceramic layer 104) and is located on the forward end side GS in the longitudinal direction HN relative to the second forward end 101BS of the second ceramic portion 101B. As a result, a corona discharge (gaseous discharge) can be generated without fail by using a simple structure. In addition, in the particulate sensor 1, the ions CP generated around the exposed portion 112B of the discharge electrode member 110 flow, together with the introduced exhaust gas EGI, toward the auxiliary electrode portion 122 located on the forward end side GS of the particulate sensor 1. Therefore, the floating ions CPF can be properly collected by the auxiliary electrode portion 122.

In addition, in the particulate sensor 1 of the present embodiment, the auxiliary electrode portion 122 is provided within the ceramic substrate 101 (ceramic laminate). This configuration prevents the insulating resistance between the auxiliary electrode portion 122 and the discharge electrode member 110, etc., from decreasing due to adhesion of water or soot.

Further, in the particulate sensor 1 of the present embodiment, the ceramic element 100 (ceramic structure) is formed by integral firing of its constituent members. Therefore, it is possible to manufacture a ceramic element 100 in which the discharge electrode member 110, the auxiliary electrode member 120, and the heater 130 are reliably integrated with the ceramic substrate 101 (ceramic laminate).

Modification:

Next, a modification of the above-described embodiment will be described. In the particulate sensor 1 of the embodiment, the ceramic element 100 includes not only the discharge electrode member 110 but also the auxiliary electrode member 120 having the auxiliary electrode portion 122. A particulate sensor 1A of the present modification differs from the particulate sensor 1 in that a ceramic element 100A which does not include the auxiliary electrode member 120 (auxiliary electrode portion 122) is used (see FIG. 2).

Notably, since the ceramic element 100A does not have the auxiliary electrode member 120, the auxiliary potential lead wire 162 and the auxiliary potential terminal 75 are not provided in the particulate sensor 1A of the modification. The ceramic element 100A differs from the particulate sensor 1 of the embodiment in this point as well. However, in the following description, an explanation of the overall mechanical structure of the particulate sensor 1A is omitted, and the ceramic element 100A of the present modification will be described with reference to FIGS. 7 and 8.

Figure 7:
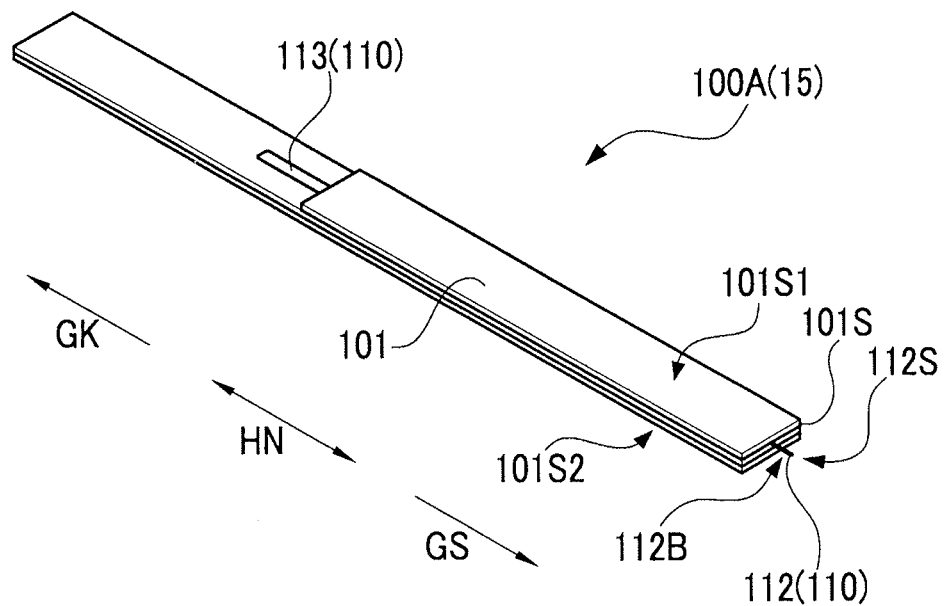
FIG. 7 is a perspective view relating to a modification and showing the entirety of the ceramic element.
Figure 8:
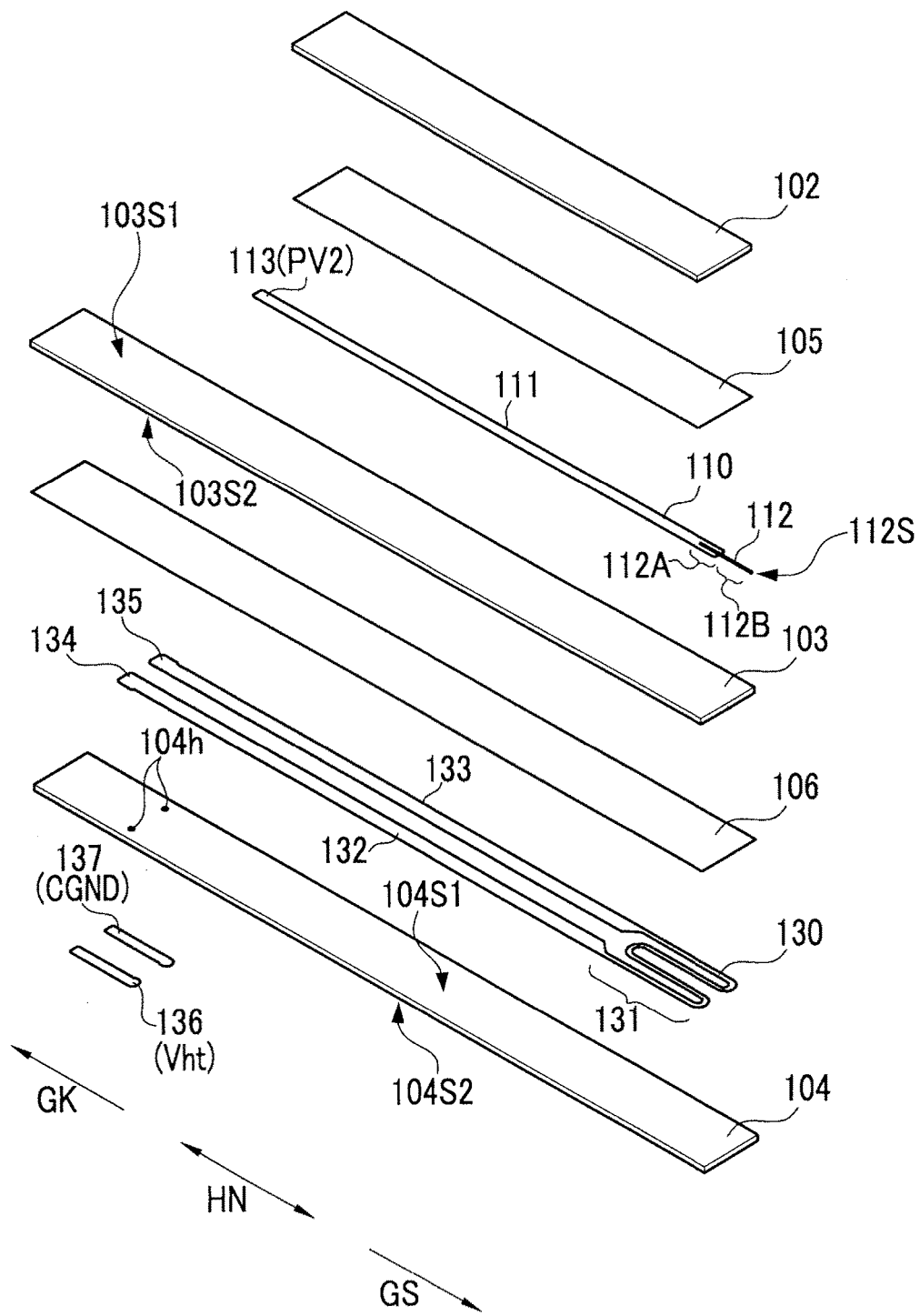
FIG. 8 is an exploded perspective view relating to the modification and showing the structure of the ceramic element.

As shown in FIGS. 7 and 8, the ceramic element 100A according to the present modification has a plate-shaped insulative ceramic substrate 101 formed of alumina. A discharge electrode member 110 and a heater 130 are embedded in the ceramic substrate 101, and are integrated by firing (integral firing).

More specifically, the ceramic substrate 101 is a ceramic laminate in which three plate-shaped ceramic layers 102, 103, and 104 formed of alumina originating from an alumina green sheet are layered together. Specifically, two insulating cover layers 105 and 106 of alumina are formed between these layers by printing. As shown in FIG. 8, the ceramic layer 102, the insulating cover layer 105, the ceramic layer 103, the insulating cover layer 106, and the ceramic layer 104 are layered in this order. The discharge electrode member 110 is disposed between the ceramic layer 102 and the ceramic layer 103; more specifically, between the insulating cover layer 105 and the ceramic layer 103. The heater 130 is disposed between the ceramic layer 103 and the ceramic layer 104; more specifically, between the insulating cover layer 106 and the ceramic layer 104. The layers, the member, and the heater are integrated, whereby the ceramic element 100A (ceramic structure) is formed. The exposed portion 112B of the discharge electrode member 110 generates ions CP by corona discharge.

As in the above-described embodiment, the discharge electrode member 110 extends in the longitudinal direction HN, and has a needle-shaped electrode portion 112 formed of platinum wire, a lead portion 111 in electrical contact with the needle-shaped electrode portion 112 and formed on one surface 103S1 of the ceramic layer 103 by pattern printing, and a discharge potential pad 113 in electrical contact with the lead portion 111.

The lead portion 111 of the discharge electrode member 110 and an embedment portion 112A (on the rear end side GK) of the needle-shaped electrode portion 112 connected to the lead portion 111 are inter-layer portions which are covered by the insulating cover layer 105 and the ceramic layer 102 and are embedded in the ceramic substrate 101 (ceramic laminate); specifically, between the ceramic layer 102 and the ceramic layer 103. Meanwhile, an exposed portion 112B (on the forward end side GS) of the needle-shaped electrode portion 112 formed of platinum wire projects from an end surface 101S of the ceramic substrate 101 located on the forward end side in the longitudinal direction HN and connecting two main faces 101S1 and 101S2 of the ceramic substrate 101. The exposed portion 112B projects into the space outside the ceramic substrate 101. A distal end portion of the exposed portion 112B is a tapered, needle-shaped distal end portion 112S. The discharge potential pad 113 is not covered by the insulating cover layer 105 and the ceramic layer 102, and is exposed on the surface 103S1 of the ceramic layer 103 of the ceramic substrate 101 at a position on the rear end side GK. As in the case of the above-described embodiment, the discharge potential terminal 73 is in physical and electrical contact with the discharge potential pad 113. A constant DC voltage is applied to the discharge potential pad 113 so as to maintain the discharge electrode member 110 at a predetermined discharge potential PV2 (see FIG. 8).

As in the case of the above-described embodiment, the heater 130 is formed on the one surface 104S1 of the ceramic layer 104 by pattern printing. The heater 130 has a heat generation portion 131 which is disposed on the forward end side GS of the ceramic element 100A and heats the exposed portion 112B of the needle-shaped electrode portion 112 of the discharge electrode member 110 when energized. Also, two heater lead portions 132 and 133 are in electrical contact with the heat generation portion 131 and extend toward the rear end side GK of the ceramic element 100A. The heater 130 is formed on the one surface 104S1 of the ceramic layer 104, and is covered by the insulating cover layer 106.

The heater lead portions 132 and 133 of the heater 130 have end portions 134 and 135 on the rear end side GK. The end portions 134 and 135 are in electrical contact, by means of through holes 104h extending through the ceramic layer 104, with a first heater pad 136 and a second heater pad 137, respectively, which are formed on the other surface 104S2 of the ceramic layer 104. Notably, as in the case of the above-described embodiment, the first heater terminal 76 is in electrical contact with the first heater pad 136, and the second heater terminal 77 is in electrical contact with the second heater pad 137. The first heater potential Vht generated by pulse control of the battery voltage is applied to the first heater pad 136, and the second heater pad 137 is maintained at the chassis GND potential CGND (see FIG. 8).

In the present modification, as described above, the auxiliary electrode member 120 is not provided in the ceramic element 100A, unlike the ceramic element 100 of the embodiment.

In the particulate sensor 1A using the ceramic element 100A according to the present modification as well, a corona discharge can be generated by applying the constant DC discharge potential PV2 to the needle-shaped distal end portion 112S of the discharge electrode member 110. Therefore, the present modification can achieve an action and effects similar to those of the embodiment; for example, the structure of the circuit section 190 becomes simple and inexpensive.

Also, since the exposed portion 112B of the discharge electrode member 110 projects from the end surface 101S of the plate-shaped ceramic substrate 101 (ceramic laminate), corona discharge (gaseous discharge) can be generated without fail between the exposed portion 112B and the inner protector 45 (reference potential member) using a simple structure.

The present invention has been described based on the embodiment and modifications thereof. However, needless to say, the present invention is not limited to the above-described embodiment and modification, etc., and may be freely modified without departing from the scope of the invention.

For example, in the above-described embodiment and modification, the ceramic substrate 101 (ceramic laminate) which constitutes the ceramic element 100, 100A is a plate-shaped substrate in which the plurality of ceramic layers 102, 103, and 104 are laminated.

Figure 9:
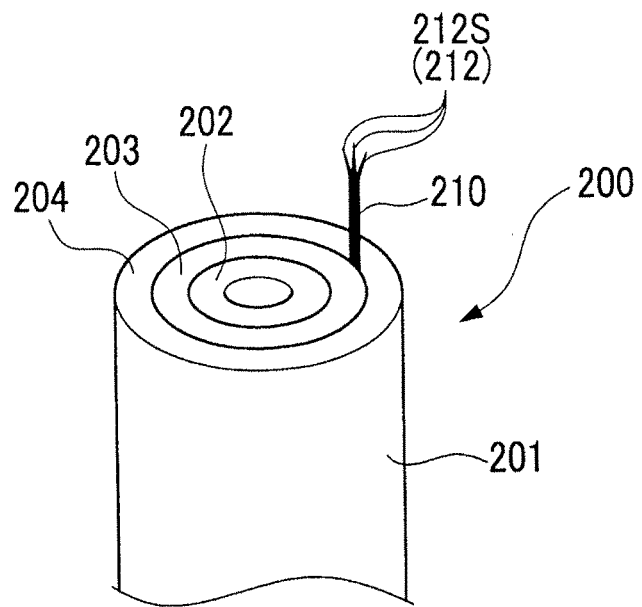
FIG. 9 is an enlarged partial perspective view showing a forward end portion of a circular columnar ceramic element.
Figure 10:
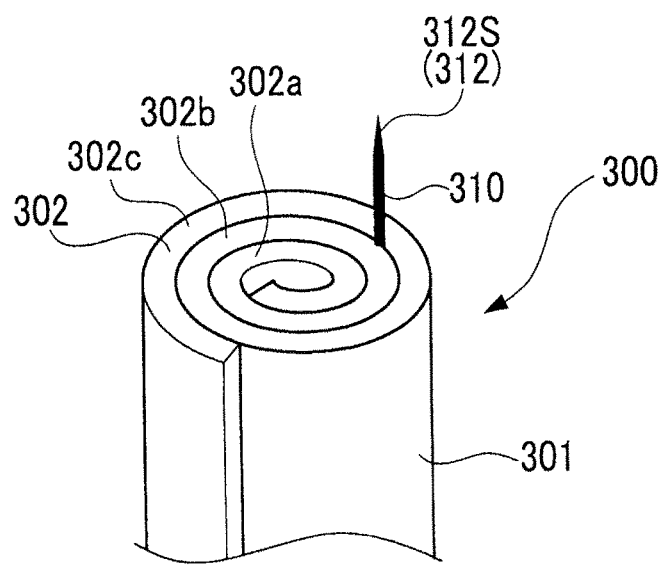
FIG. 10 is an enlarged partial perspective view showing a forward end portion of a cylindrical tubular ceramic element.

However, the ceramic element (ceramic structure) is not limited to those having a plate-like shape, and may have a circular columnar shape or a circular tubular shape. FIGS. 9 and 10 show circular columnar and circular tubular ceramic elements 200 and 300. In the circular columnar ceramic element 200 shown in FIG. 9, a circular columnar ceramic laminate 201 is formed by layering a plurality of ceramic layers 202, 203, and 204 in such a manner that annular rings similar to the annual rings of a tree are formed, and a discharge electrode member 210 (a needle-shaped electrode portion 212 having needle-shaped distal end portions 212S) is provided in the ceramic laminate 201 so that the discharge electrode member 210 is located between the ceramic layers 203 and 204 and projects outward. In the circular tubular ceramic element 300 shown in FIG. 10, a circular tubular ceramic laminate 301 is formed by spirally winding a single ceramic sheet 302 in such a manner that a plurality of ceramic layers 302a, 302b, and 302c are layered in the radial direction, and a discharge electrode member 310 (a needle-shaped electrode portion 312 having a needle-shaped distal end portion 312S) is provided in the ceramic laminate 301 so that the discharge electrode member 310 is located between the ceramic layers 302b and 302c and projects outward.

In the above-described embodiment and modification, the needle-shaped electrode portion 112 of the discharge electrode member 110, including the exposed portion 112B, is formed of platinum wire. However, the material of the needle-shaped electrode portion is not limited to metal wire, and the needle-shaped electrode portion may be formed by bending a metal plate into a predetermined shape.

Also, the material of the needle-shaped electrode portion is not limited to platinum, and metallic materials which are excellent in oxidation resistance, such as noble metal alloys (e.g., platinum alloy), may be used. Also, in the embodiment and the modification, a single needle-shaped distal end portion is provided using platinum wire. However, as shown in FIG. 9, the needle-shaped electrode portion 212 may be formed from a metallic plate so as to provide a plurality of needle-shaped distal end portions 212S.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2014-001920 filed Jan. 8, 2014, incorporated herein by reference in its entirety.

What is claimed is:

1. A particulate sensor which includes an ion source configured for generating ions by corona discharge and a reference potential member disposed around the ion source and maintained at a reference potential, wherein ions generated by the corona discharge adhere to particulates contained in a gas under measurement so as to generate positively charged particulates, the reference potential member also serving as a collection electrode is maintained at a collection potential and collects floating ions which are some of the ions generated by the ion source that have not adhered to the particulates, and the particulate sensor detects particulates contained in a gas under measurement by means of a current signal corresponding to a charge amount of ions discharged from the sensor in the form of the positively charged particulates, wherein the ion source comprises a ceramic structure which includes:

a ceramic laminate of a plurality of insulative ceramic layers, the ceramic laminate extending in a longitudinal direction and having a rear end side and a forward end side; and a discharge electrode member formed at the forward end side of the ceramic laminate having an inter-layer portion embedded between two of the ceramic layers of the ceramic laminate and an exposed portion extending from the inter-layer portion to a position outside the ceramic laminate, the discharge electrode member generating the corona discharge between the reference potential member and the exposed portion when a constant DC discharge potential is applied to the discharge electrode member, wherein the exposed portion of the discharge electrode member has one or a plurality of needle-shaped distal end portions which project into a space outside the ceramic laminate without contacting the ceramic laminate and which generate the corona discharge, and wherein the reference potential member comprises a tubular member which surrounds the forward end side of the ceramic laminate from a radially outer side, the tubular member including introduction holes for introducing the gas under measurement into a space within the tubular member and around the ceramic laminate and a discharge opening for discharging the introduced gas under measurement formed in a forward end side of the tubular member.

2. A particulate sensor as claimed in claim 1, wherein the ceramic structure has a heater which is disposed in the ceramic laminate and heats the exposed portion of the discharge electrode member when energized.

3. A particulate sensor as claimed in claim 1, wherein the ceramic structure has an auxiliary electrode portion which is maintained at an auxiliary potential and assists in collection of the floating ions by the collection electrode.

4. The particulate sensor as claimed in claim 3, wherein the auxiliary electrode portion is disposed within the ceramic laminate and is located on a forward end side of the ceramic laminate in the longitudinal direction;

the exposed portion of the discharge electrode member is disposed within the ceramic laminate and is located on a rear end side of the ceramic laminate in the longitudinal direction; and when the particulate sensor is in use, the gas under measurement flows around a portion of the ceramic laminate, the portion extending from the exposed portion to the auxiliary electrode portion, from the rear end side toward the forward end side in the longitudinal direction.

5. The particulate sensor as claimed in claim 1, wherein the auxiliary electrode portion is disposed within the ceramic laminate and is located on a forward end side of the ceramic laminate in the longitudinal direction;

the exposed portion of the discharge electrode member is disposed within the ceramic laminate and is located on a rear end side of the ceramic laminate in the longitudinal direction; and when the particulate sensor is in use, the gas under measurement flows around a portion of the ceramic laminate, the portion extending from the exposed portion to the auxiliary electrode portion, from the rear end side toward the forward end side in the longitudinal direction.

6. A particulate sensor as claimed in claim 4, wherein the ceramic laminate includes:

a first ceramic portion extending in the longitudinal direction and composed of a plurality of ceramic layers; and a second ceramic portion layered on the first ceramic portion, composed of one or a plurality of ceramic layers, and being shorter than the first ceramic portion in the longitudinal direction, a second forward end of the second ceramic portion which is an end of the second ceramic portion located on the forward end side in the longitudinal direction being offset toward the rear end side in the longitudinal direction from a first forward end of the first ceramic portion which is an end of the first ceramic portion located on the forward end side in the longitudinal direction, wherein the exposed portion of the discharge electrode member projects from the second forward end of the second ceramic portion; and the auxiliary electrode portion is provided in the first ceramic portion and is located on the forward end side in the longitudinal direction in relation to the second forward end of the second ceramic portion.

7. A particulate sensor as claimed in claim 5, wherein the ceramic laminate includes:

a first ceramic portion extending in the longitudinal direction and composed of a plurality of ceramic layers; and a second ceramic portion layered on the first ceramic portion, composed of one or a plurality of ceramic layers, and being shorter than the first ceramic portion in the longitudinal direction, a second forward end of the second ceramic portion which is an end of the second ceramic portion located on the forward end side in the longitudinal direction being offset toward the rear end side in the longitudinal direction from a first forward end of the first ceramic portion which is an end of the first ceramic portion located on the forward end side in the longitudinal direction, wherein the exposed portion of the discharge electrode member projects from the second forward end of the second ceramic portion; and the auxiliary electrode portion is provided in the first ceramic portion and is located on the forward end side in the longitudinal direction in relation to the second forward end of the second ceramic portion.

8. The particulate sensor as claimed in claim 1, wherein the ceramic laminate has a plate-like shape and has two main faces; and the exposed portion of the discharge electrode member projects from an end surface of the ceramic laminate which connects the main faces of the ceramic laminate.

9. The particulate sensor as claimed in claim 2, wherein the ceramic laminate has a plate-like shape and has two main faces; and the exposed portion of the discharge electrode member projects from an end surface of the ceramic laminate which connects the main faces of the ceramic laminate.

10. The particulate sensor as claimed in claim 1, wherein the ceramic structure is formed by integral firing of its constituent members.

11. A particulate sensor which includes an ion source configured for generating ions by corona discharge and a reference potential member disposed around the ion source and maintained at a reference potential, wherein ions generated by the corona discharge adhere to particulates contained in a gas under measurement so as to generate positively charged particulates, the reference potential member also serving as a collection electrode is maintained at a collection potential and collects floating ions which are some of the ions generated by the ion source that have not adhered to the particulates, and the particulate sensor detects particulates contained in a gas under measurement by means of a current signal corresponding to a charge amount of ions discharged from the sensor in the form of the positively charged particulates, wherein the ion source comprises a ceramic structure which includes:

a ceramic laminate of a plurality of insulative ceramic layers, the ceramic laminate extending in a longitudinal direction and having a rear end side and a forward end side; and a discharge electrode member formed at the forward end side of the ceramic laminate having an inter-layer portion embedded between two of the ceramic layers of the ceramic laminate and an exposed portion extending from the inter-layer portion to a position outside the ceramic laminate, the discharge electrode member generating the corona discharge between the reference potential member and the exposed portion when a constant DC discharge potential is applied to the discharge electrode member, wherein the exposed portion of the discharge electrode member has one or a plurality of needle-shaped distal end portions which project into a space outside the ceramic laminate and which generate the corona discharge, wherein an entirety of the one or a plurality of needle-shaped distal end portions does not contact the laminate, wherein the exposed portion comprises a metal wire or a metal plate, and wherein the reference potential member comprises a tubular member which surrounds the forward end side of the ceramic laminate from a radially outer side, the tubular member including introduction holes for introducing the gas under measurement into a space within the tubular member and around the ceramic laminate and a discharge opening for discharging the introduced gas under measurement formed in a forward end side of the tubular member.

12. A particulate sensor which includes an ion source configured for generating ions by corona discharge and a reference potential member disposed around the ion source and maintained at a reference potential, wherein ions generated by the corona discharge adhere to particulates contained in a gas under measurement so as to generate positively charged particulates, and the particulate sensor detects particulates contained in a gas under measurement by means of a current signal corresponding to a charge amount of ions discharged from the sensor in the form of the positively charged particulates, wherein the ion source comprises a ceramic structure which includes:

a ceramic laminate of a plurality of insulative ceramic layers; and a discharge electrode member having an inter-layer portion embedded between two of the ceramic layers of the ceramic laminate and an exposed portion extending from the inter-layer portion to a position outside the ceramic laminate, the discharge electrode member generating the corona discharge between the reference potential member and the exposed portion when a constant DC discharge potential is applied to the discharge electrode member, wherein the exposed portion of the discharge electrode member has one or a plurality of needle-shaped distal end portions which project into a space outside the ceramic laminate without contacting the ceramic laminate and which generate the corona discharge, said particulate sensor further comprising a collection electrode which is maintained at a collection potential and collects floating ions which are some of the ions generated by the ion source that have not adhered to the particulates, wherein the ceramic structure has an auxiliary electrode portion which is maintained at an auxiliary potential and assists in collection of the floating ions by the collection electrode, the ceramic laminate extends in a longitudinal direction;

the auxiliary electrode portion is disposed within the ceramic laminate and is located on a forward end side of the ceramic laminate in the longitudinal direction;

the exposed portion of the discharge electrode member is disposed within the ceramic laminate and is located on a rear end side of the ceramic laminate in the longitudinal direction; and when the particulate sensor is in use, the gas under measurement flows around a portion of the ceramic laminate, the portion extending from the exposed portion to the auxiliary electrode portion, from the rear end side toward the forward end side in the longitudinal direction.

13. A particulate sensor which includes an ion source configured for generating ions by corona discharge and a reference potential member disposed around the ion source and maintained at a reference potential, wherein ions generated by the corona discharge adhere to particulates contained in a gas under measurement so as to generate positively charged particulates, and the particulate sensor detects particulates contained in a gas under measurement by means of a current signal corresponding to a charge amount of ions discharged from the sensor in the form of the positively charged particulates, wherein the ion source comprises a ceramic structure which includes:

a ceramic laminate of a plurality of insulative ceramic layers; and a discharge electrode member having an inter-layer portion embedded between two of the ceramic layers of the ceramic laminate and an exposed portion extending from the inter-layer portion to a position outside the ceramic laminate, the discharge electrode member generating the corona discharge between the reference potential member and the exposed portion when a constant DC discharge potential is applied to the discharge electrode member, wherein the exposed portion of the discharge electrode member has one or a plurality of needle-shaped distal end portions which project into a space outside the ceramic laminate without contacting the ceramic laminate and which generate the corona discharge, said particulate sensor further comprising a collection electrode which is maintained at a collection potential and collects floating ions which are some of the ions generated by the ion source that have not adhered to the particulates, wherein the ceramic structure has an auxiliary electrode portion which is maintained at an auxiliary potential and assists in collection of the floating ions by the collection electrode, wherein the reference potential member also serves as the collection electrode, the ceramic laminate extends in a longitudinal direction;

the auxiliary electrode portion is disposed within the ceramic laminate and is located on a forward end side of the ceramic laminate in the longitudinal direction;

the exposed portion of the discharge electrode member is disposed within the ceramic laminate and is located on a rear end side of the ceramic laminate in the longitudinal direction; and when the particulate sensor is in use, the gas under measurement flows around a portion of the ceramic laminate, the portion extending from the exposed portion to the auxiliary electrode portion, from the rear end side toward the forward end side in the longitudinal direction.

* * * * *